(12) United States Patent
Godlewski et al.

(10) Patent No.: US 8,568,468 B2
(45) Date of Patent: Oct. 29, 2013

(54) STENT-GRAFT COMPRISING AT LEAST ONE REINFORCED HOLE

(75) Inventors: Richard J. Godlewski, Bloomington, IN (US); Tony C. Hopkins, Bloomington, IN (US); Shyam S V Kuppurathanam, Bloomington, IN (US); Julie E. Urbanski, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 157 days.

(21) Appl. No.: 12/325,437

(22) Filed: Dec. 1, 2008

(65) Prior Publication Data

US 2009/0149939 A1 Jun. 11, 2009

Related U.S. Application Data

(60) Provisional application No. 60/992,833, filed on Dec. 6, 2007.

(51) Int. Cl.
*A61F 2/06* (2013.01)

(52) U.S. Cl.
USPC .................................................... 623/1.13

(58) Field of Classification Search
USPC .............. 623/1.23, 112, 1.12–1.16; 606/1.98, 606/200, 198
See application file for complete search history.

(56) References Cited

U.S. PATENT DOCUMENTS

| | | |
|---|---|---|
| 5,665,115 A | 9/1997 | Cragg |
| 5,693,089 A | 12/1997 | Inoue |
| 5,782,904 A | 7/1998 | White et al. |
| 5,824,037 A | 10/1998 | Fogarty et al. |
| 5,824,042 A | 10/1998 | Lombardi et al. |
| 5,824,061 A | 10/1998 | Quijano et al. |
| 6,004,347 A | 12/1999 | McNamara et al. |
| 6,395,019 B2 | 5/2002 | Chobotov |
| 6,626,938 B1 | 9/2003 | Butaric et al. |
| 6,699,277 B1 * | 3/2004 | Freidberg et al. ............ 623/1.13 |
| 6,768,058 B2 * | 7/2004 | Pallapothu .................... 174/652 |
| 2003/0088305 A1 * | 5/2003 | Van Schie et al. ........... 623/1.12 |
| 2003/0176912 A1 * | 9/2003 | Chuter et al. ................ 623/1.13 |
| 2004/0060723 A1 * | 4/2004 | Pallapothu .................. 174/65 G |
| 2005/0149165 A1 * | 7/2005 | Thistle ......................... 623/1.13 |
| 2005/0159803 A1 * | 7/2005 | Lad et al. ..................... 623/1.13 |
| 2005/0197690 A1 * | 9/2005 | Molaei et al. ................ 623/1.13 |
| 2006/0142840 A1 | 6/2006 | Sherry et al. |
| 2007/0112410 A1 * | 5/2007 | Butaric et al. ............... 623/1.13 |
| 2010/0016946 A1 * | 1/2010 | McDermott ................. 623/1.13 |

FOREIGN PATENT DOCUMENTS

DE 19754747 12/1997

\* cited by examiner

*Primary Examiner* — Ryan Severson
*Assistant Examiner* — Ashley Fishback
(74) *Attorney, Agent, or Firm* — Brinks Hofer Gilson & Lione

(57) ABSTRACT

The present embodiments provide a stent-graft for use in a medical procedure that includes a graft having at least first and second reinforced holes disposed in the graft. The first and second reinforced holes may include first and second grommets. In one embodiment, a first stent may be coupled to the graft using at least one suture disposed through the first and second grommets. Alternatively, a first stent may be coupled to the graft, such that the first stent itself is disposed through the first and second grommets. The grommets may include self-sealing properties to reduce leakage around the sutures and/or stent segments that are disposed through the grommets.

17 Claims, 4 Drawing Sheets

STENT-GRAFT COMPRISING AT LEAST ONE REINFORCED HOLE

PRIORITY CLAIM

This invention claims the benefit of priority of U.S. Provisional Application Ser. No. 60/992,833, entitled "Stent-Graft Comprising at Least One Reinforced Hole," filed Dec. 6, 2007, the disclosure of which is hereby incorporated by reference in its entirety.

BACKGROUND

The present invention relates generally to apparatus and methods for treating medical conditions, and more specifically, to stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used in different procedures in conjunction with a graft material to form a stent-graft, for example, to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. In a stent made of a shape-memory alloy such as nitinol, the shape-memory alloy may be employed to cause the stent to return to a predetermined configuration upon removal of the sheath or other device maintaining the stent in its predeployment configuration.

With balloon-expandable stents, the stent may be delivered and deployed using a catheter having proximal and distal ends and one or more balloons disposed on the catheter. The stent may be coupled to the balloon during insertion until the target site is reached, and then deployed by inflating the balloon to expand the stent to bring the stent into engagement with the target site. Alternatively, the stent may be placed separately in the vessel and a subsequent catheter having an expansion portion may then be inserted into the stent to expand the stent at the target site.

Stents also may comprise a variety of configurations. For example, stents may comprise a wire-mesh, coil or helical shape, or a slotted tube configuration. One commonly-employed stent design is known as a "Z-stent" or Gianturco stent. The Gianturco stent may comprise a series of substantially straight segments interconnected by a series of bent segments. The bent segments may comprise acute bends or apices. The stent is arranged in a zigzag configuration in which the straight segments are set at angles relative to each other and are connected by the bent segments.

When stents are employed as part of a stent-graft, the stent commonly is attached to the graft using one or more sutures. Typically, the sutures are hand-sewn around the stent and directly through the graft at multiple locations to secure the stent to the graft. Such suturing techniques may be labor intensive. Further, the formation of suture holes in the graft may increase the risks of endoleaks through the graft, particularly since the size of such suture holes may increase over time.

Various other stent-graft designs have used different techniques to couple the stent to the graft. For example, in some designs the stent may be sandwiched or laminated between two graft layers, where the graft layers are adhered directly to one another to secure the stent therebetween. While such alternative techniques may not puncture the graft, manufacturing complexities may arise and such stent-grafts may comprise an increased profile due to the provision of multiple graft layers.

In view of the above, it would be desirable to provide a stent-graft that secures a stent to a graft, while reducing the likelihood of endoleaks through the graft.

SUMMARY

The present embodiments provide a stent-graft for use in a medical procedure that comprises a graft having at least first and second reinforced holes disposed in the graft. The first and second reinforced holes may comprise first and second grommets. In one example, a first stent may be coupled to the graft using at least one suture disposed through the first and second grommets. The suture may be threaded through adjacent grommets such that the suture is alternately disposed internal and external to the graft.

The first stent may comprise a generally zig-zag shape. A plurality of grommets may be arranged in a generally zig-zag pattern around a circumference of the graft, wherein the generally zig-zag pattern corresponds to the zig-zag shape of the first stent. Therefore, the stent and grommets generally are aligned, but need not necessarily overlap one another. For example, the first stent may comprise at least one first segment forming a strut, and adjacent grommets may be disposed on opposing sides of the strut to cause the suture to be threaded around the strut. By threading the suture through the grommets, the suture used to couple the first stent to the graft does not directly puncture the graft.

In another example, at least a portion of the first stent is disposed through the first and second grommets to couple the first stent to the graft. The first stent may be threaded through adjacent grommets such that the first stent is alternately disposed internal and external to the graft. The first stent may comprise first and second ends, whereby the first end of the stent is threaded through multiple grommets and subsequently adhered to the second end of the stent. This example does not require the use of any sutures.

Advantageously, endoleaks may be reduced around the sutures and/or stent segments that are disposed through the grommets. In one embodiment, inner regions of the grommets may be sized for snug engagement with the sutures and/or stent segments. Alternatively, the grommets may have self-sealing properties. For example, at least one resilient membrane may be configured to substantially sealingly engage the sutures and/or stent segments. In each instance, neither suture nor stent material is directly threaded through the graft, which may reduce endoleaks while ensuring that the size of holes in the graft will not increase over time.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
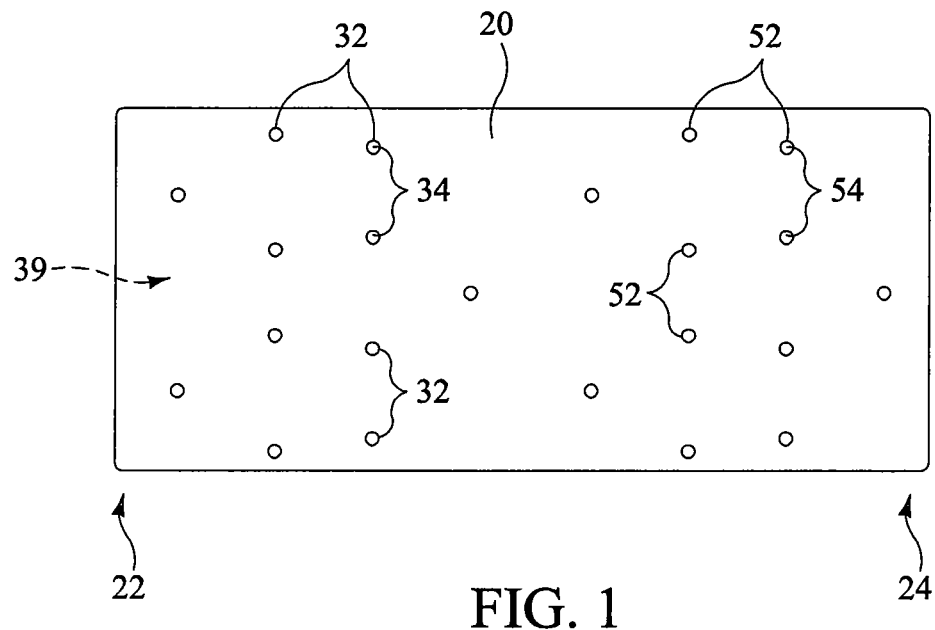
FIG. 1 is a side view of a graft.

Referring now to FIG. 1, a graft 20 is shown prior to formation into a stent-graft. The graft 20 generally comprises a proximal end 22 and a distal end 24. The graft 20 may form a generally cylindrical configuration and comprises a lumen 39 suitable for passing fluid between the proximal and distal ends 22 and 24.

Many different types of graft materials may be used for the graft 20. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues, including small intestine submucosa (SIS).

In accordance with one aspect, at least one reinforced hole is disposed at a predetermined location in the graft. Preferably, multiple reinforced holes are provided, where the multiple reinforced holes form a pattern that at least partially corresponds to the cylindrical shape of one or more stents.

In one example, the reinforced holes comprise grommets designed to reinforce the holes. While grommets generally are shown for illustrative purposes below, other alternative reinforcements may be provided. For example, the holes in the graft may be configured using a reinforced suture arrangement commonly employed in button holes. Therefore, regardless of the reinforcement employed, the holes in the graft are reinforced in a manner that may reduce the likelihood of endoleaks and/or reduce the likelihood that the size of the holes may increase over time.

In FIG. 1, a plurality of predetermined locations 32 and 52 are shown. A first series of predetermined locations 32 are selected, which may correspond to placement of a first stent 30, as will be explained below with respect to FIGS. 3-4. Similarly, a second series of predetermined locations 52 are selected, which may correspond to placement of a second stent 50.

A first pattern may be associated with the first series of predetermined locations 32, and a second pattern may be associated with the second series of predetermined locations 52. The first pattern may be disposed near the proximal end 22 of the graft 20, while the second pattern may be disposed near the distal end 24 of the graft 20. The first and second patterns may be substantially identical, as depicted in FIG. 1. Alternatively, the first and second patterns may be different, for example, if the shapes of first and second stents 30 and 50 are different, as explained further below.

Figure 2:
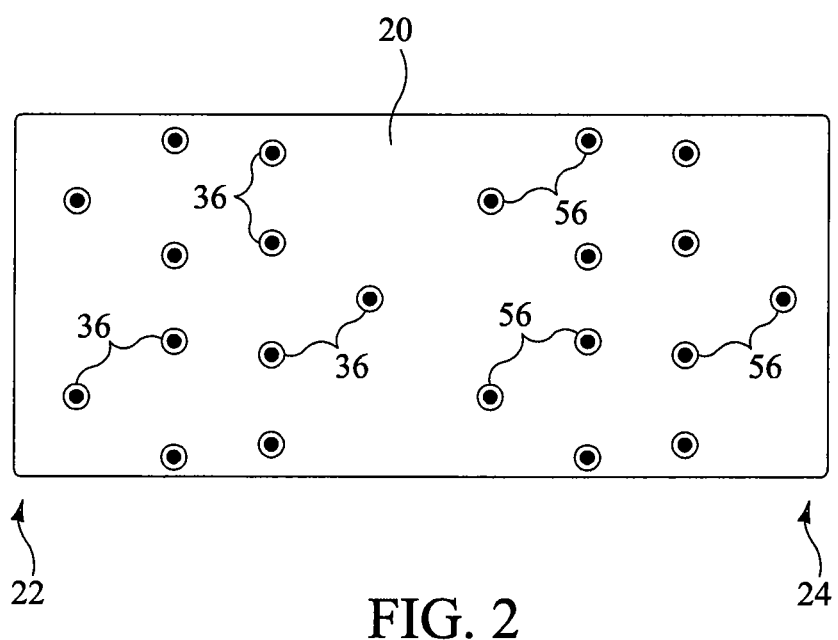
FIG. 2 is a side view of the graft of FIG. 1 comprising a plurality of reinforced holes.

As shown in FIG. 1, a first plurality of holes 34 may be formed through the graft 20 at the first series of predetermined locations 32. A plurality of grommets 36 may be disposed through each of the associated holes 34 and secured to the graft 20, as shown in FIG. 2. Similarly, a second plurality of holes 54 may be formed through the graft 20 at the second series of predetermined locations 52, and then a plurality of grommets 56 may be disposed through each of the associated holes 54 and secured to the graft 20. The grommets 36 and 56 may comprise any suitable grommet shape and configuration, and preferably comprise self-sealing features, as explained in further detail with respect to FIGS. 7-8 below. Moreover, each of the grommets 36 and 56 may be secured to the graft 20 using any suitable manufacturing technique, for example, using commercially available grommet-inserting punches and dies, as explained further below.

Figure 3:
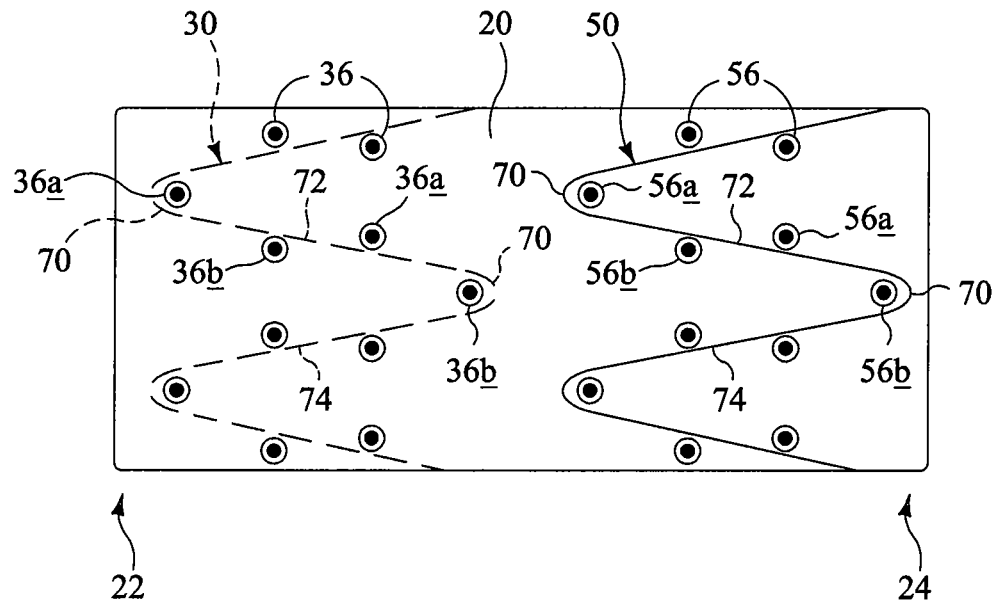
FIG. 3 is a side view of the graft of FIGS. 1-2 having at least one stent aligned prior to being coupled to the graft.

Referring now to FIG. 3, after the plurality of grommets 36 and 56 have been formed in the graft 20, at least one stent may be coupled to the graft. As shown in FIG. 3, first and second stents 30 and 50 are provided and correspond to plurality of grommets 36 and 56, respectively.

First and second stents 30 and 50 may be substantially identical in shape, as shown in FIG. 3. In this example, the stents 30 and 50 generally comprise zig-zag shapes. The stents 30 and 50 may be formed from a single wire comprising a plurality of substantially straight first segments 72 and second segments 74 having a plurality of bent segments 70 disposed therebetween. As shown in FIG. 3, the first stent 30 is sized and configured to be disposed internal to the graft 20, while the second stent 50 is sized and configured to be disposed external to the graft 20.

During manufacture, the first stent 30 may be compressed to a diameter smaller than an inner diameter of the graft 20, then the first stent 30 may be advanced distally within the graft 20 to a location that may substantially overlap with, or be disposed adjacent to, the plurality of grommets 36, as shown in FIG. 3. The second stent 50 then may be disposed over the graft 30 at a location distal to the first stent 30, and may be positioned to substantially overlap with, or be disposed adjacent to, the plurality of grommets 56.

Figure 4:
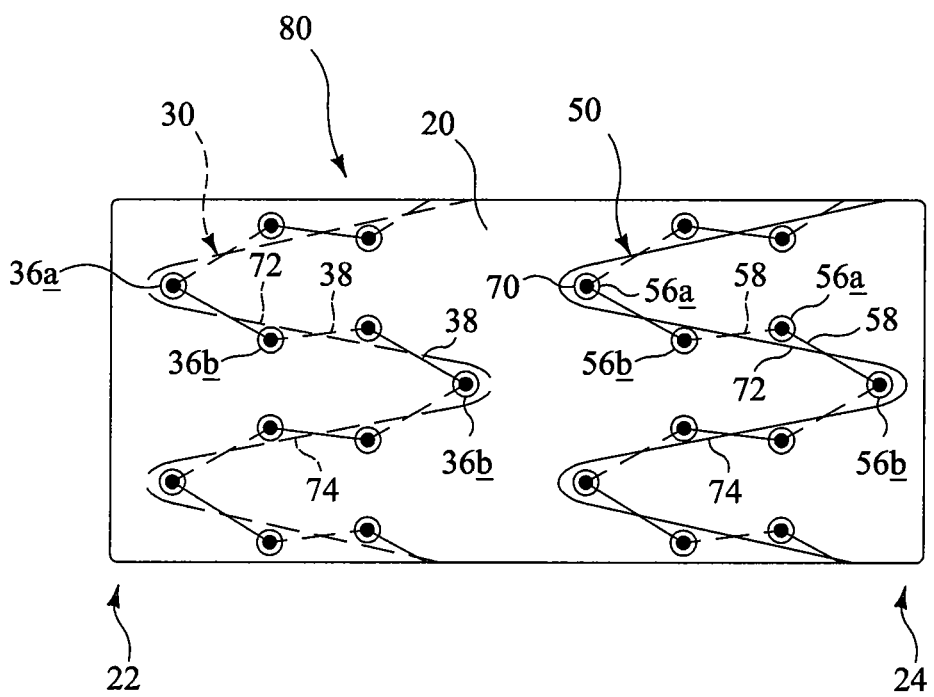
FIG. 4 is a side view depicting at least one stent coupled to the graft of FIGS. 1-3.

Referring now to FIG. 4, the first stent 30 may be coupled to the graft 20 by threading one or more sutures 38 through one or more of the grommets 36. As shown in FIG. 4, a first suture 38 is threaded through each of the grommets 36, such that in this example, the suture 38 is continuous and consists of a single piece of suture material, which may be any type of suture material known to one of skill in the art including single or multiple stranded suture material. Between a first set of adjacent grommets 36a and 36b, the first suture 38 may be disposed external to the graft 20, and between the next series of adjacent grommets, the first suture 38 then may be disposed internal to the graft 20, as depicted in FIG. 4. In effect, the first suture 38 is weaved through each of the adjacent grommets 36a and 36b one at a time. Once the threading of the first suture 38 is completed, first and second ends of the first suture 38 may be connected together, for example, by tying a knot. In this manner, the first stent 30 may be securely coupled to the graft 20.

Similarly, the second stent 50 may be coupled to the graft 20 by threading a second suture 58 through each of the grommets 56. Between a first set of adjacent grommets 56a and

56b, the second suture 58 may be disposed external to the graft 20, and between the next series of adjacent grommets, the second suture 58 then may be disposed internal to the graft 20, as depicted in FIG. 4. First and second ends of the second suture 58 also may be connected together, for example, by tying a knot, to securely couple the second stent 50 to the graft 20. Therefore, a finished stent-graft 80 may be formed, as shown in FIG. 4.

Adjacent grommets may be disposed on opposing sides of the struts of the stents. For example, adjacent grommets 36a and 36b may be disposed on opposing sides of the first segments 72 and the second segments 74, as shown in FIG. 4. Accordingly, the suture must pass over the struts of the first and second segments 72 and 74 multiple times, thereby enhancing attachment of the first stent 30 to the graft 20. Similarly, adjacent grommets 56a and 56b may be disposed on opposing sides of the first and second segments 72 and 74 of the second stent 50, thereby enhancing the attachment of the second stent 50 to the graft 20.

Various types of sutures 38 and 58 may be used. For example, synthetic sutures may be made from polypropylene, nylon, polyamide, polyethylene, and polyesters such as polyethylene terephthalate. These materials may be used as monofilament suture strands, or as multifilament strands in a braided, twisted or other multifilament construction. Regardless of the type of suture employed, it is capable of being used to sew the stents 30 and 50 to the graft 20.

In one embodiment, the pattern associated with the grommets 36 and 56 may correspond to the shapes of the first and second stents 30 and 50, respectively. For example, where stents 30 and 50 comprise generally zig-zag shaped stents, the grommets may be disposed in a pattern to at least partially correspond to the zig-zag shape, as generally depicted in FIGS. 2-4. Here, the pattern of the grommets is not identical to the zig-zag shape of the stent, but rather, adjacent grommets 36a and 36b are positioned on opposing sides of the stent 30, as noted above, thereby facilitating attachment of the suture 38 around the stent 30.

Further, the pattern associated with the grommets 36 and 56 may be variable or uniform. FIGS. 2-4 depict an example of a uniform grommet pattern. In each instance, a single grommet is disposed just beneath a corresponding bent segment 70 of the stent 30. Further, two adjacent grommets 36a and 36b are disposed on opposing sides of each of the first and second segments 72 and 74. Therefore, the uniform grommet pattern comprises four substantially aligned columns of grommets 36 disposed circumferentially about the stent 20, a depicted in FIGS. 2-4.

Alternatively, a variable pattern may be provided, for example, where only some of the bent segments 70 comprise associated grommets and/or where a variable number of grommets are associated with each of the first and second segments 72 and 74. Still further, a random grommet pattern may be disposed in the graft 20, i.e., the grommet pattern may not correspond to the structure of the stent.

In further alternatives, the first and second stents 30 and 50 may comprise shapes other than zig-zag shapes. Solely by way of example, one or more of the stents 30 or 50 may be circumferentially wound in a continuous fashion to form a coil or helical wire structure. The coil or helical wire structure may be disposed internal or external to the graft 20. In this embodiment, the grommets 36 and 56 may be arranged in a generally corresponding coil or helical pattern about the circumference of the graft 20, thus facilitating threading of the suture around portions of the coil or helical wire structure.

Grommets 36 and 56 may reduce endoleaks by reducing the amount of fluid that may flow between the sutures 38 and 58 and their associated grommets. For example, the grommets 36 and 56 may comprise inner diameters that are sized to snugly engage an exterior surface of the suture material. Additionally, the grommets may comprise self-sealing features, such as a resilient membrane configured to snugly engage an exterior surface of the sutures, as described further below with respect to FIGS. 7-8. Advantageously, the stent-graft 80 may have significantly fewer endoleaks relative to conventional stent-grafts that are manufactured by threading the sutures directly through the graft.

The stents 30 and 50 each have reduced diameter delivery states in which they may be advanced to a target location within a vessel, duct or other anatomical site. The stents 30 and 50 further have expanded deployed states in which they may be configured to apply a radially outward force upon the vessel, duct or other target location, e.g., to maintain patency within a passageway, or the stents simply may be used to hold open the graft 20 for example, to treat an aneurysm. In the expanded state, fluid flow is allowed through the central lumen 39 of the stent-graft 80.

The stents 30 and 50 may be manufactured from a shape memory material, for example nitinol, a nickel titanium alloy. If manufactured from nitinol, the stent-graft 80 may assume the expanded state shown in FIG. 4 upon removal of a suitable delivery sheath. Alternatively, the stents 30 and 50 may be manufactured from an annealed elastic-plastic material, such as 305L stainless steel. With this material, the stent-graft 80 may be deployed via balloon expansion.

In yet further alternative embodiments, the stents 30 and 50 may be made from other metals and alloys that allow the stents 30 and 50 to return to their original, expanded configurations upon deployment. Solely by way of example, the stents 30 and 50 may comprise other materials such as cobalt-chrome alloys, amorphous metals, tantalum, platinum, gold and titanium. The stents 30 and 50 also may be made from non-metallic materials, such as thermoplastics and other polymers. Optionally, the stent-graft 80 may comprise at least one barb that may be formed integrally as part of one or more struts of the stents 30 and 50, or may comprise an external barb that is adhered to a surface of one or more struts of the stents.

Finally, it should be noted that while first and second stents 30 and 50 are illustratively coupled to the graft 20, only one stent may be employed, or three or more stents may be coupled to the graft 20. Further, the graft 20 may comprise a bifurcated configuration having a trunk portion and first and second leg portions, whereby one or more stents are coupled to the trunk and/or leg portions using the techniques described herein.

Figure 5:
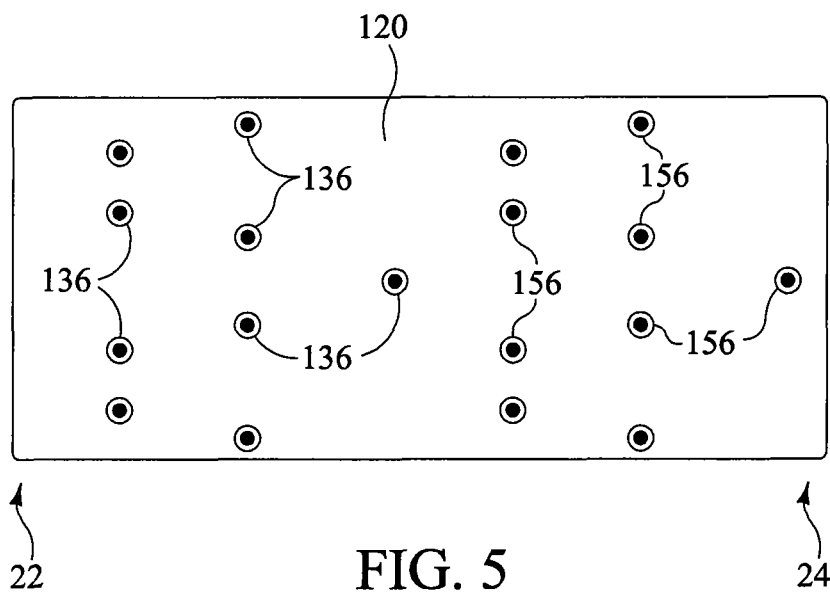
FIG. 5 is a side view of an alternative graft comprising a plurality of reinforced holes.
Figure 6:
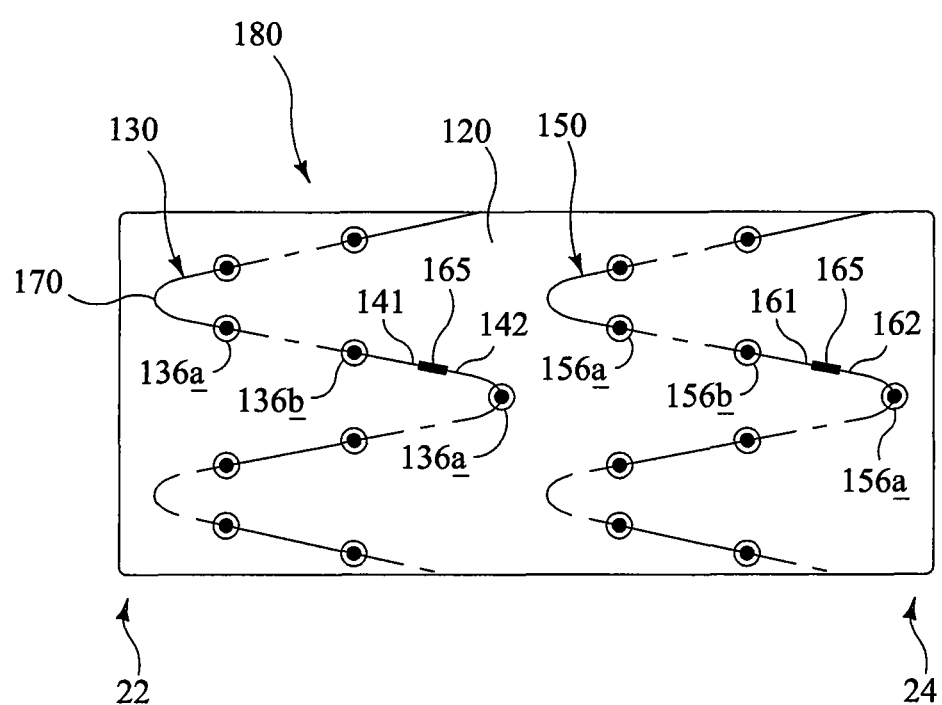
FIG. 6 is a side view depicting at least one stent coupled to the graft of FIG. 5.

Referring now to FIGS. 5-6, one or more stents may be coupled to a graft 120 directly via one or more reinforced holes, such as grommets, formed in the graft. In FIG. 5, a first series of grommets 136 and a second series of grommets 156 are formed in the graft 120. The grommets 136 and 156 may be provided in accordance with the grommets 36 and 56, as described above with respect to FIGS. 1-4. Moreover, each of the grommets 136 and 156 may be secured to the graft 120 using any suitable technique, for example, using commercially available grommet-inserting punches and dies, as explained further below with respect to FIGS. 7-8.

Referring now to FIG. 6, after the plurality of grommets 136 and 156 have been formed in the graft 120, at least one stent may be coupled to the graft. As shown in FIG. 6, first and second stents 130 and 150 are provided and correspond to the plurality of grommets 136 and 156, respectively.

The first stent 130 may comprise a wire member having a first end 141 and a second end 142. The first stent 130 may be coupled to the graft 120 by threading the first end 141 through one or more of the grommets 136. As shown in FIG. 6, the first end 141 is threaded through each of the grommets 136. Between a first set of adjacent grommets 136a and 136b, a portion of the first stent 130 may be disposed external to the graft 120, and between the next series of adjacent grommets, another portion of the first stent 130 may be disposed internal to the graft 120, as depicted in FIG. 6. In effect, the first end 141 of the stent 130 is weaved through each of the adjacent grommets 136a and 136b one at a time. Once the threading of the stent is completed, the first end 141 of the stent may be joined with the second end 142 of the stent 130 using any suitable technique, such as using a weld or solder 165. In this manner, the stent 130 may be coupled to the graft 120 without the use of sutures.

Similarly, the second stent 150 may comprise a wire member having a first end 161 and a second end 162, and may be coupled to the graft 120 by threading the first end 161 through one or more of the grommets 156. In effect, the first end 161 of the stent 150 may be weaved through each of the adjacent grommets 156a and 156b one at a time, and once the threading of the stent is completed, the first end 161 of the stent may be joined with the second end 162 of the stent, as shown in FIG. 6. A completed stent-graft 180 therefore is formed.

In accordance with one aspect, the grommet pattern may substantially correspond with the circumferential shape of the stents 130 and 150, i.e., the plurality of grommets 136 and 156 may be arranged in a substantially zig-zag pattern. By providing grommets arranged in a substantially zig-zag pattern, a zig-zag shaped stent may be disposed through the grommets without placing increased stress upon the stent struts.

The bent regions 170 of the stents 130 and 150 may be disposed through grommets, or alternatively, the bent regions 170 may be spaced apart from the grommets. In FIG. 6, a combination of each technique is shown, whereby apices of the bent regions 170 closer to the proximal end 22 of the graft 120 are spaced apart from the proximally-disposed grommets, while apices of the bent regions 170 closer to the distal end 24 are aligned substantially with the distally-disposed grommets.

Grommets 136 and 156 may be designed to reduce endoleaks by reducing the amount of fluid that may flow between the stents 130 and 150 and the grommets. For example, the grommets 136 and 156 may comprise inner diameters that are sized to snugly engage an exterior surface of the stents 130 and 150. Additionally, the grommets may comprise self-sealing features, such as a resilient membrane configured to snugly engage an exterior surface of the stents 130 and 150, as described further below with respect to FIGS. 7-8. Advantageously, endoleaks between the grommets and the stents may be reduced.

The stent-graft 80 and the stent-graft 180 may be delivered into a vessel, duct, or other anatomical site using a suitable deployment system or introducer. An introducer, such as that described in PCT application WO98/53761, entitled "A Prosthesis and a Method and Means of Deploying a Prosthesis," which is incorporated herein by reference in its entirety, may be used to deploy the stent-grafts. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. Further, such delivery devices may be compact and may have a relatively uniform, low-diameter radial profile, allowing for atraumatic access and delivery.

Figure 7:
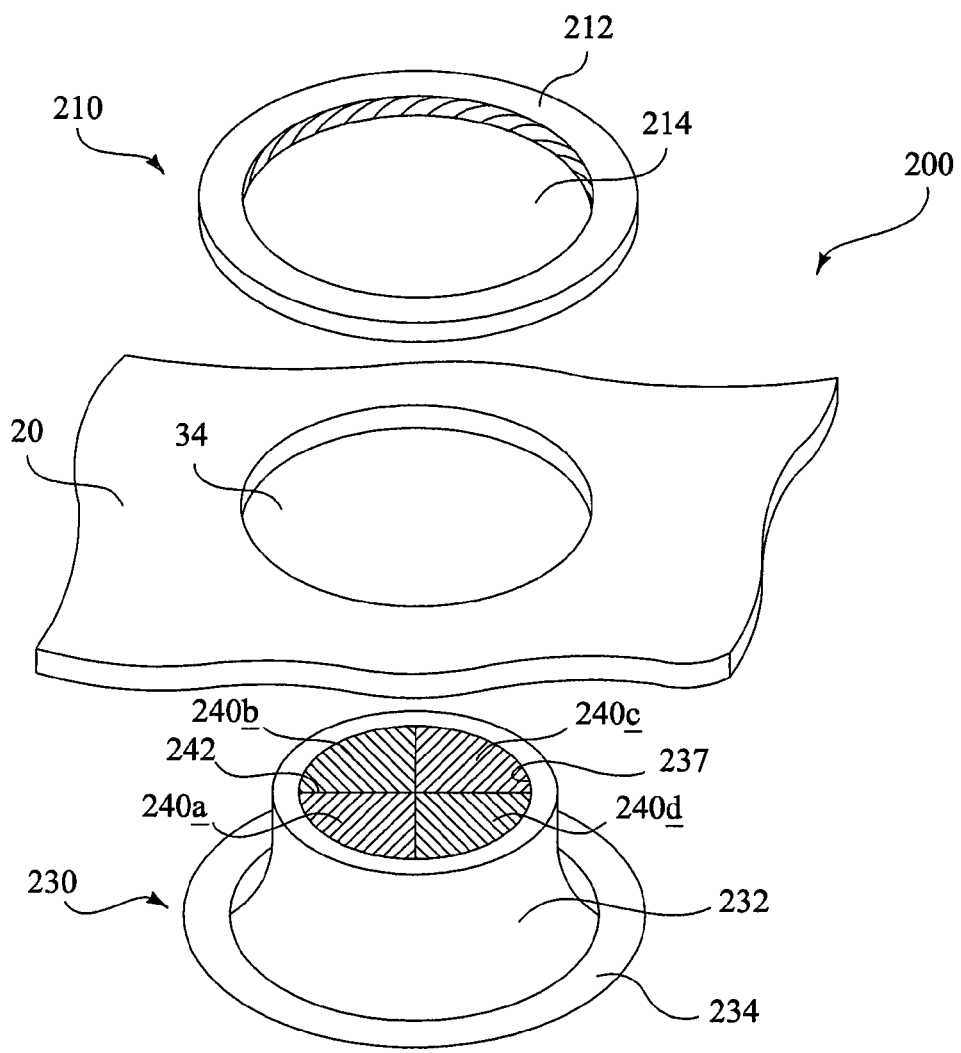
FIG. 7 is a perspective view of a grommet suitable for use with a graft.

Referring now to FIG. 7, an exemplary grommet 200, suitable for use with the stent-grafts 80 and 180, is described. Grommet 200 may comprise first and second members 210 and 230. First member 210 may comprise a ring-shaped body 212 having a bore 214 formed therein. Second member 230 may comprise an upright portion 232 having a flanged portion 234.

During manufacture, a plurality of holes 34 are formed in the graft 20, as shown in FIG. 7 and explained above with respect to FIG. 1. The holes may be formed using any suitable apparatus, whether manual or mechanical, such as a mechanical hole punch. An inner diameter is associated with each hole 34. The upright portion 232 of the second member 230 may be inserted through the hole 34, preferably until the flanged portion 234 abuts a lower surface of the graft 20. The second member 230 of the grommet 200 and the graft 20 then may be placed on a suitable surface, such as an associated die (not shown). The first member 210 then may be placed over the upright portion 232 of the second member 230 to sandwich the graft 20 therebetween. In a next step, a setting tool, such as a punch device, may be inserted through the first member 210, the graft 20, and the second member 230. When the setting tool is actuated, e.g., by striking the punch device with a hammer, the edges of the flanged portion 234 may be curled around the ring-shaped body 212 of the first member 210, thereby securing the grommet 200 to the graft 20. As will be apparent, various other grommet structures may be employed, and other techniques may be used to secure the grommet 200 to the graft 20. Moreover, any of grommets 36, 56, 136 and 156, described in the embodiments above, may be provided in accordance with the exemplary grommet 200, or alternatively may be manufactured using other grommet arrangements.

Advantageously, endoleaks may be reduced around the sutures and/or stent segments that are disposed through the grommets. In one example, the endoleaks may be reduced based primarily on the sizing of an inner region 237 of the grommet 200, i.e., the inner region 237 of the grommet may comprise a relatively snug engagement with the sutures and/or stent segments, thereby reducing endoleaks.

Figure 8:
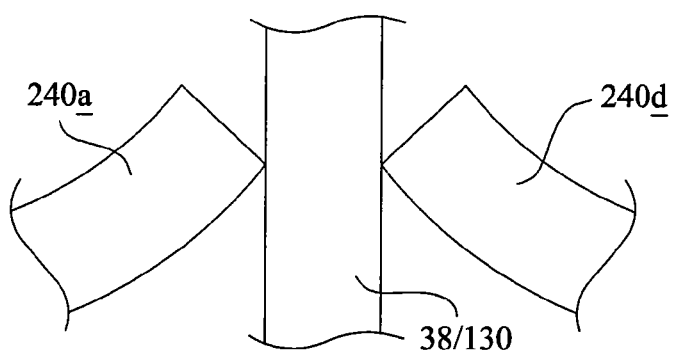
FIG. 8 is a side view illustrating features associated with the grommet of FIG. 7.

Additionally, the grommet 200 may comprise self-sealing properties, for example, at least one resilient membrane configured to substantially sealingly engage the stent or sutures. In the example of FIGS. 7-8, the resilient membrane comprises four resilient members 240a-240d, which may be coupled to the inner region 237 of the second member 230. The resilient members 240a-240d may be separated by one or more slits 242, as shown in FIG. 7, such that little or no fluid is allowed to pass through the membrane. The membrane is resilient enough to allow the passage of the suture 38 or the stent 130 therethrough, as shown in FIG. 8, and then preferably is self-sealing around the suture 38 or the stent 130. The membrane may be formed from any suitable material, such as biocompatible rubber. In this manner, endoleaks between the grommets and the suture 38 or the stent 130 may be significantly reduced, as depicted in FIG. 8.

Therefore, by coupling a stent to a graft having reinforced holes, such as grommets, using the techniques described herein, neither suture nor stent material is directly threaded through the graft, which may reduce endoleaks while ensuring that the size of holes in the graft will not increase over time.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent-graft comprising:
    a graft having proximal and distal ends;
    at least first and second reinforced holes disposed in the graft and reinforced relative to surrounding material of the graft, wherein the at least first and second reinforced holes are disposed longitudinally along a length of the graft; and
    a first stent coupled to the graft, where the first stent is coupled to the graft using a first continuous suture that is woven through the first and second reinforced holes, wherein the first continuous suture consists of a single piece of suture material.

2. The stent-graft of claim 1 wherein the at least first and second reinforced holes comprise at least first and second grommets.

3. The stent-graft of claim 2, wherein the first continuous suture is threaded through the at least first and second grommets such that the first continuous suture is alternately disposed internal and external to the graft.

4. The stent-graft of claim 2 wherein at least one of the grommets comprises self-sealing properties.

5. The stent-graft of claim 4 wherein the at least one grommet comprises at least one resilient membrane configured to substantially sealingly engage the first continuous suture.

6. The stent-graft of claim 1 wherein the first stent comprises a generally zig-zag shape.

7. The stent-graft of claim 6 where the at least first and second reinforced holes are part of a plurality of reinforced holes arranged in a generally zig-zag pattern around a circumference of the graft, wherein the generally zig-zag pattern corresponds to the zig-zag shape of the first stent.

8. The stent-graft of claim 7 wherein the first stent comprises at least one first segment forming a strut, wherein adjacent reinforced holes are disposed on opposing sides of the strut to cause the first continuous suture to be threaded around the strut.

9. A stent-graft comprising:
    a graft having proximal and distal ends;
    at least first and second reinforced holes disposed in the graft and reinforced relative to surrounding material of the graft, wherein the at least first and second reinforced holes are disposed longitudinally along a length of the graft; and
    a first stent coupled to the graft without the use of sutures, where a first continuous stent strut of the first stent is woven through the first and second reinforced holes.

10. The stent-graft of claim 9 wherein the at least first and second reinforced holes comprise at least first and second grommets.

11. The stent-graft of claim 10, wherein the first continuous stent strut is threaded through the at least first and second grommets such that the first continuous stent strut is alternately disposed internal and external to the graft.

12. The stent-graft of claim 11 wherein the first stent comprises first and second ends, and wherein the first end of the stent is adapted to be threaded through the multiple grommets and subsequently adhered to the second end of the stent.

13. The stent-graft of claim 10 wherein at least one of the grommets comprises self-sealing properties.

14. The stent-graft of claim 13 wherein the at least one grommet comprises at least one resilient membrane configured to substantially sealingly engage the first continuous stent strut.

15. The stent-graft of claim 10 further comprising a second stent, wherein the stent-graft further comprises:
    a first series of reinforced holes disposed around a portion of the graft, wherein the first continuous stent strut of the first stent is disposed through the first series of reinforced holes to couple the first stent to the graft; and
    a second series of reinforced holes disposed around a portion of the graft, wherein a first continuous stent strut of the second stent is disposed through the second series of reinforced holes to couple the second stent to the graft.

16. The stent-graft of claim 9 wherein the first stent comprises a generally zig-zag shape.

17. The stent-graft of claim 16 wherein the at least first and second reinforced holes are part of a plurality of reinforced holes arranged in a generally zig-zag pattern around a circumference of the graft that generally corresponds to the zig-zag shape of the first stent.

* * * * *